US006698592B2

(12) United States Patent
Kenning et al.

(10) Patent No.: US 6,698,592 B2
(45) Date of Patent: *Mar. 2, 2004

(54) VIRTUAL IMPACTOR

(75) Inventors: Vanessa M. Kenning, Kennewick, WA (US); Christopher L. Moler, Richland, WA (US); Joseph G. Birmingham, Vancouver, WA (US); Patrick T. Call, West Richland, WA (US)

(73) Assignee: MesoSystems Technology, Inc., Kennewick, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/202,210

(22) Filed: Jul. 22, 2002

(65) Prior Publication Data

US 2002/0179499 A1 Dec. 5, 2002

Related U.S. Application Data

(63) Continuation of application No. 09/955,481, filed on Sep. 17, 2001, which is a continuation-in-part of application No. 09/494,962, filed on Jan. 13, 2000, now Pat. No. 6,290,065, which is a continuation-in-part of application No. 09/191,980, filed on Nov. 13, 1998, now Pat. No. 6,062,392.

(51) Int. Cl.[7] .............................................. B07B 7/04
(52) U.S. Cl. ..................................................... 209/143
(58) Field of Search ................................ 209/143, 142, 209/146, 147, 134, 135, 139.1; 55/462; 95/31, 32, 33

(56) References Cited

U.S. PATENT DOCUMENTS

| | | |
|---|---|---|
| 877,460 A | 1/1908 | Brunner et al. |
| 902,958 A | 11/1908 | Galusha |

(List continued on next page.)

FOREIGN PATENT DOCUMENTS

| | | | |
|---|---|---|---|
| DE | 13 10 913 U | 9/1934 | |
| DE | 2 260 729 | 5/1974 | |
| EP | 0 543 108 A1 | 5/1993 | |
| FR | 626 191 | 8/1927 | |
| WO | WO 98/58725 | 12/1998 | ........... B01D/45/08 |

OTHER PUBLICATIONS de la Mora, J.F. 1988. "Aerodynamic Focusing of Particles and Heavy Molecules: First Annual Report." *NTIS* (Feb.): 16 pp.

de la Mora, J.F. 1990. "Aerodynamic Focusing of Particles and Heavy Molecules: Final Report." *NTIS* (Jan.): 12 pp.

de la Mora, J.F. 1996. "Drastic Improvement of the Resolution of Aerosol Size Spectrometers via Aerodynamic Focusing: The Case of Variable Pressure Impactors." *Chemical Engineering Communications* 151: 101–24.

*Primary Examiner*—Donald P. Walsh
*Assistant Examiner*—Joseph C Rodriguez
(74) *Attorney, Agent, or Firm*—Ronald M. Anderson

(57) ABSTRACT

A separation plate separates a major flow of fluid from a minor flow of fluid. The major flow includes a minor portion of particles greater than a "cut size," while the minor flow includes a major portion of particles greater than the cut size. Plates define a laterally extending passage between a front of the separation plate and its rear. The passage telescopes or converges from an initial height at its inlet, to a substantially smaller height at its outlet. A slot extends transversely into the plates from within a minor flow portion of the passage and connect into major flow outlet ports. The flow of fluid into the outlet is thus divided into the major flow, which flows from the major flow outlet ports and the minor flow that exits the outlet of the passage. To accommodate a desired flow of fluid, the width of the passage can be changed, or an array of stacked separation plates can be employed.

31 Claims, 8 Drawing Sheets

U.S. PATENT DOCUMENTS

| | | |
|---|---|---|
| 906,038 A | 12/1908 | Terry |
| 1,603,878 A | 10/1926 | Smith |
| 1,807,378 A | 5/1931 | Budil |
| 1,825,274 A | 9/1931 | Leach |
| 2,939,545 A | 6/1960 | Silverman |
| 3,693,457 A | 9/1972 | Pilat |
| 3,754,868 A | 8/1973 | Witz et al. |
| 3,901,798 A | 8/1975 | Peterson |
| 3,932,151 A | 1/1976 | Lau |
| 3,983,743 A | 10/1976 | Olin et al. |
| 4,133,202 A | 1/1979 | Marple |
| 4,301,002 A | 11/1981 | Loo |
| 4,321,822 A | 3/1982 | Marple et al. |
| 4,387,603 A | 6/1983 | Nelson |
| 4,452,068 A | 6/1984 | Loo |
| 4,640,140 A | 2/1987 | Burghoffer et al. |
| 4,670,135 A | 6/1987 | Marple et al. |
| 4,689,052 A | 8/1987 | Ogren et al. |
| 4,697,462 A | 10/1987 | Daube, Jr. et al. |
| 4,764,186 A | 8/1988 | Langer |
| 4,767,524 A | 8/1988 | Yeh et al. |
| 4,877,430 A | 10/1989 | Gutermuth |
| 4,941,899 A | 7/1990 | Liu |
| 4,942,297 A | 7/1990 | Johnson et al. |
| 4,972,957 A | 11/1990 | Liu et al. |
| 4,990,740 A | 2/1991 | Meyer |
| 5,040,424 A | 8/1991 | Marple et al. |
| 5,128,539 A | 7/1992 | Rodgers et al. |
| 5,254,861 A | 10/1993 | Carpenter et al. |
| 5,318,609 A | 6/1994 | Kittler |
| 5,332,550 A | 7/1994 | Booker |
| 5,412,975 A | 5/1995 | Raabe et al. |
| 5,425,802 A | 6/1995 | Burton et al. |
| 5,472,645 A | 12/1995 | Rock et al. |
| 5,498,271 A | 3/1996 | Marple et al. |
| 5,512,216 A | 4/1996 | Rock et al. |
| 5,533,406 A | 7/1996 | Geise |
| 5,776,754 A | 7/1998 | Caldwell |
| 5,786,894 A | 7/1998 | Shields et al. |
| 5,788,741 A | 8/1998 | Burton et al. |
| 5,858,043 A | 1/1999 | Geise |
| 5,967,332 A | 10/1999 | Geise |
| 6,062,392 A | 5/2000 | Birmingham et al. |
| 6,110,247 A | 8/2000 | Birmingham et al. |

OTHER PUBLICATIONS de la Mora, J.F. 1988. "Aerodynamic Focusing of Particles in a Carrier Gas." *Journal of Fluid Mechanics* 195 (Oct.): 1–21.

Fernandez–Feria, R. et al. 1990 "Brownian–Motion Limited Aerodynamic Focusing of Heavy Molecules." *Rarefied Gas Dynamics: Proceedings of the 17th International Symposium on Rarefied Gas Dynamic* (Jul.): 214–21.

Fuerstenau, S. et al. 1994. "Visualization of Aerodynamically Focused Subsonic Aerosol Jets." *Journal of Aerosol Science:* 25:1 (Jan.) 165–73.

Hochrainer, D. 1973. "Measurement of Aerosol Particle Size Distribution with an Improved Spectral Impactor." *NTIS:* N7323533 26pp.

Liu, P. et al. 1996. "Optimizing the Detection Efficiency of a Low Pressure, In–Situ Particle Monitor Using Aerodynamic Focusing Lenses." *Proceedings—Institute of Environmental Science:* 217–24.

Jurcik, B. et al. 1995. "On the Shape of Impactor Efficiency Curves." *Journal of Aerosol Science:* 26:7 1139–47.

Patent Cooperation Treaty Search Report. PCT–US98–12471, Corona Catalysis Corporation et al. Oct. 14, 1998.

Vance, Richard F. "Slanted Baffle Mist Eliminator." *U.S. Statutory Invention:* Registration No. H1499. Nov. 7, 1995.

VIRTUAL IMPACTOR

RELATED APPLICATIONS

This application is a continuation application, based on prior application Ser. No. 09/955,481, filed on Sep. 17, 2001, which is a continuation-in-part of (Ser. No. 09/494,962) U.S. Pat. No. 6,290,065, filed on Jan. 31, 2000, which itself is a continuation-in-part of (Ser. No. 09/191,980) U.S. Pat. No. 6,062,392, filed on Nov. 13, 1998, the benefit of the filing dates of which are hereby claimed under 35 U.S.C. §120.

GOVERNMENT RIGHTS

This invention was made with government support under Contract No. DAAM01-97-M-0006 and Contract No. DAAD13-99-D-0008, awarded by the U.S. Department of Defense. The government has certain rights in this invention.

FIELD OF THE INVENTION

This invention pertains to the field of separating particles from a fluid stream, and more particularly to a combination of a nozzle and virtual impactor steps used to separate a particle-laden fluid stream into a portion containing a substantially greater concentration of particles and another portion containing substantially fewer particles.

BACKGROUND OF THE INVENTION

The separation and collection of particles/aerosols from an airstream or other fluid streams are of concern in two contexts: first, for purposes of analyzing the type and concentration of such particles/aerosols entrained in the fluid and, second, for clearing particles/aerosols from the fluid stream. Additionally, it is sometimes important to classify particles entrained in a fluid stream by size. For example, this technology may be employed in the detection of airborne biological or chemical warfare agents, the detection of biological contamination in confined spaces, such as aircraft or hospitals, or the detection of industrial pollutants (either in ambient fluid or in the effluent of smokestacks).

Much effort has been expended in the past in the detection and classification of particles or aerosols in fluid streams. Impactors have been used for collecting aerosol particles for many decades. In the earliest embodiments, a stream of fluid containing the particles was accelerated toward an impactor plate. Due to their inertia, the particles hit the impactor plate and were collected there while the fluid was deflected to the side. With these types of impactors, only heavy particles were collected while particles below a certain "cut size" were carried away by the fluid stream.

However, a significant cause of inaccuracy in such impactors results from the deposition of particles on surfaces of the impactor other than the intended collection surfaces. This phenomenon reduces the accuracy of measurement of total particle mass concentration and of the size-fractionation of particles, since such losses cannot be accurately estimated for aerosols having varying size, shape, or chemistry. Additionally, particles may either become re-entrained in the fluid stream or bounce from the impactor's collection surface upon impact. To remedy this problem, "virtual" impactors have been developed that separate particles from a fluid stream by forces other than impaction. Virtual impactors may operate on a number of different principles, but all avoid actual "impact" as a means to separate particles from a fluid in which the particles are entrained and rely on differences in particle mass to induce inertial separation.

Specifically, a particle-laden fluid stream is directed toward a surface presenting an obstruction to the forward movement of the fluid stream. The surface includes a void at the point where the particles would normally impact the surface. When a major portion of the fluid stream changes direction to avoid the obstruction presented by the surface, fine particles remain entrained in the deflected major portion of the fluid stream. Heavier or more dense particles, on the other hand, fail to change direction and are collected in a region of relatively stagnant fluid (a "dead air zone") that is created near the surface. The heavier particles entrained in a minor portion of the fluid stream enter the void defined through the surface, where they can be captured or analyzed.

Some examples of virtual impactors can be found in U.S. Pat. Nos. 3,901,798; 4,670,135; 4,767,524; 5,425,802; and 5,533,406. Because typical virtual impactors do not actually collect particles themselves, but merely redirect them into two different fluid streams according to their mass, they are essentially free of the problems of particle bounce and reentrainment associated with actual impactor devices. Still, particle "wall loss," i.e., unintended deposition of particles on various surfaces of virtual impactor structures, especially at curved or bent portions, remains a challenge with many virtual impactors because typically many stages or layers of virtual impactors are required to complete particle separation.

Therefore, a need exists for a virtual impactor that separates particles from a fluid stream more efficiently and without substantial particle wall loss.

SUMMARY OF THE INVENTION

In accord with the present invention, a separation plate employed for separating a fluid stream into a major flow and a minor flow is defined. The major flow includes a minor portion of particles that are above a predetermined size, and the minor flow includes a major portion of the particles that are above the predetermined size. The separation plate includes a block in which is defined a laterally extending passage having an inlet disposed on one edge of the block and an outlet disposed on an opposite edge of the block. This laterally extending passage has a lateral dimension that is substantially greater than a transverse dimension of the passage. Opposed surfaces of the passage between which the transverse dimension of the passage is defined generally converge toward each other within the block, so that the outlet has a substantially smaller cross-sectional area than the inlet. A transverse, laterally extending slot is defined within the block and is in fluid communication with a portion of the passage that has the substantially smaller cross-sectional area. A major flow outlet port is also defined in the block, in fluid communication with the transverse, laterally extending slot. The major flow enters the slot and exiting the block through the major flow outlet port, while the minor flow exits the block through the outlet of the passage. The major flow carries the minor portion of the particles and the minor flow carries the major portion of the particles.

Another transverse, laterally extending slot is preferably disposed opposite the slot within the block; and another major flow outlet port is in fluid communication with the other slot to provide a further fluid path for the major flow carrying the minor portion of the particles.

The block preferably comprises a first plate and a second plate that are coupled together, with a passage being defined between facing surfaces of the first plate and the second plate. In addition, the facing surfaces of the first plate and the second plate are preferably joined at each end of the passage, sealing the ends of the passage. A portion of the passage is thus defined in a facing surface of the first plate, and another portion of the passage is defined in a facing surface of the second plate.

The passage converges with a defined transverse profile toward a convergent nozzle at an entrance to a minor flow portion of the passage. The slot is then disposed distally of but proximate to the convergent nozzle.

A lateral dimension of the passage is a function of a desired flow of fluid through the inlet of the passage. Alternatively, in some applications, a plurality of the separation plates can be arrayed to accommodate a desired flow of fluid.

Another aspect of the present invention is directed to a method for separating a fluid flow in which particles are entrained, generally consistent with the above description.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

In the present description, the prefix "micro" is applied generally to components that have submillimeter-sized features. Microcomponents are fabricated using micromachining techniques known in the art, such as micromilling, photolithography, deep ultraviolet (or x-ray) lithography, electrodeposition, electrodischarge machining (EDM), laser ablation, and reactive or non-reactive ion etching.

Also as used hereinafter, the following terms shall have the following definitions:

Particle—any separately identifiable solid, liquid, aerosol, or other component entrained in a fluid stream that has a greater mass than the fluid forming the fluid stream, and is the subject of separation and collection for analysis. For the purposes of the present description, mass density of particles is assumed to be approximately 1 gm/cm$^3$. It is contemplated that the particles may arise from sampling almost any source, including but not limited to, air, water, soil, and surfaces.

Fluid—any fluid susceptible to fluid flow, which may comprise liquids or gases, and which may entrain foreign particles therein. Unless otherwise noted, fluid shall mean the ambient fluid containing unconcentrated particles for collection, not the fluid into which the particles are concentrated after collection or capture.

Figure 1A:
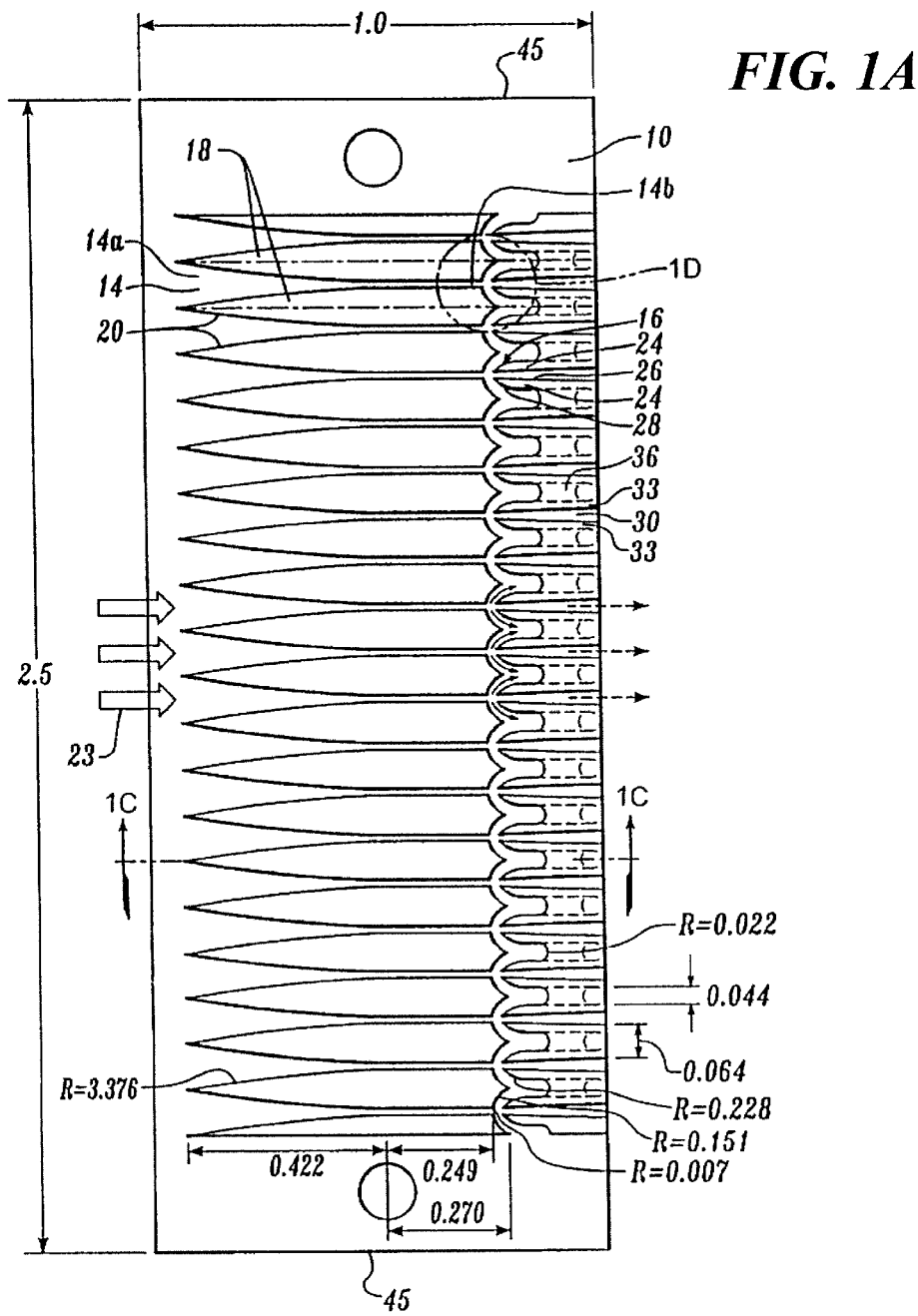
FIG. 1A is a plan view of a separation plate of the present invention.
Figure 1B:
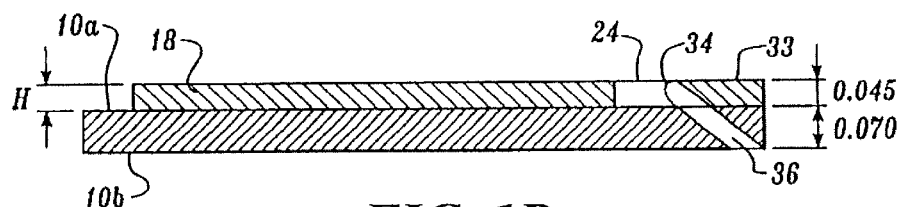
FIG. 1B is a cross-sectional view of the separation plate taken along line 1B—1B of FIG. 1A.
Figure 1C:
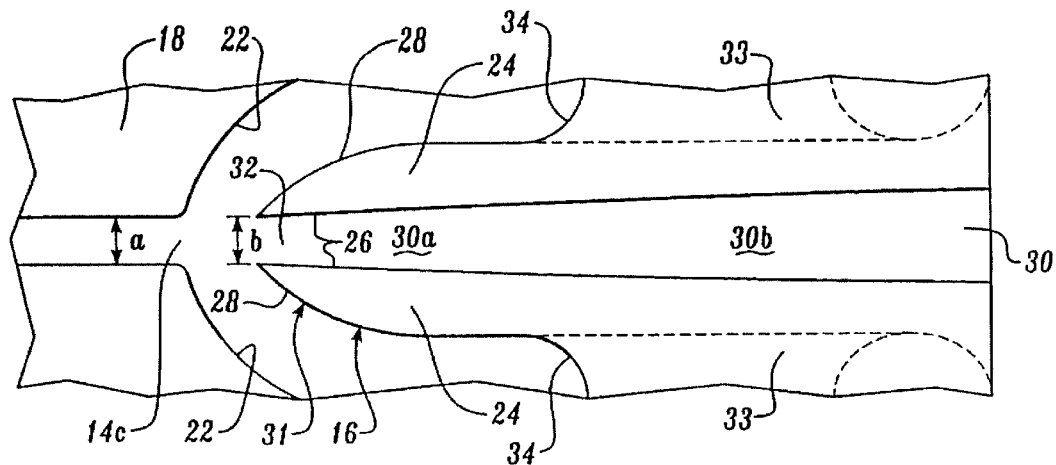
FIG. 1C is an enlarged view of a pair of a nozzle and a virtual impactor at section 1C of FIG. 1A.
Figure 1D:
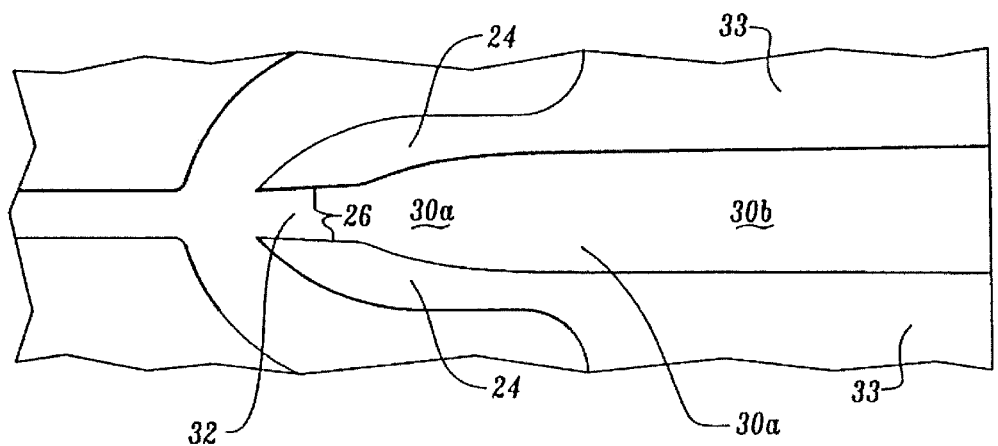
FIG. 1D is an enlarged view of another configuration of a pair of a nozzle and a virtual impactor.

FIGS. 1A, 1B, and 1C illustrate the first embodiment of a virtual impact separation plate 10 formed in accordance with the present invention. Separation plate 10 may be formed of any material suitable for micromachining, such as plastics and metals. Separation plate 10 includes a first surface 10a and an opposing second surface 10b. The first surface 10a includes plural pairs of a nozzle 14 and a virtual impactor 16 (FIG. 1C). Each nozzle 14 includes an inlet end 14a and an outlet end 14b, and is defined between adjacent nozzle projections 18 having a height "H" (FIG. 1B). Two nozzle projections 18 cooperate to define one nozzle 14. Each nozzle projection 18 includes two sidewalls 20 that are configured to define one side of a nozzle 14, which comprise a telescoping design that generally tapers from inlet end 14a to outlet end 14b. Nozzle projection 18 further includes two generally concave walls 22 at its downstream end that are positioned to provide nozzle projection 18 with a tapered downstream "tail." In contrast to a tapered downstream tail, another of the embodiments described below that is actually more preferred includes stepped transitions that reduce the size of the passage at its outlet. Throughout the present description, the terms "upstream" and "downstream" are used to refer to the direction of a fluid stream 23 flowing along the separation plate of the present invention.

Each virtual impactor 16 comprises a pair of generally fin-shaped projections 24 having height "H." Fin-shaped projection 24 includes an inner wall 26 and a generally convex outer wall 28. Inner walls 26 of fin-shaped projections 24 in a pair are spaced apart and face each other to define an upstream minor flow passage 30a therebetween. Convex outer walls 28 of the pair of fin-shaped projections 24 cooperatively present a generally convex surface 31 facing the fluid flow direction. Referring specifically to FIG. 1C, an inlet end 32 of upstream minor flow passage 30a defines a virtual impact void through convex surface 31, where "virtual" impaction occurs as more fully described below. A width of outlet end 14b of nozzle 14 is defined as "a," and a width of inlet end 32 of upstream minor flow passage 30a is defined as "b."

First surface 10a of separation plate 10 may further include a plurality of virtual impactor bodies 33 extending downstream from the downstream ends of adjacent fin-shaped projections 24 of adjacent pairs of virtual impactors 16. Each virtual impactor body 33 includes opposing external walls that extend downstream from the downstream ends of inner walls 26. External walls of adjacent virtual impactor bodies 33 are spaced apart to define a downstream minor flow passage 30b therebetween. Upstream and downstream minor flow passages 30a and 30b are aligned and communicate with each other to form a minor flow passage 30. As illustrated in FIGS. 1A, 1B, and 1C, fin-shaped projections 24 of adjacent virtual impactors 16 and a virtual impactor body 33 may be integrally formed. Optionally, an orifice 34 may be defined through virtual impactor body 33 adjacent to the downstream ends of convex outer walls 28 of adjacent virtual impactors 16. Orifices 34 define terminal ends of passageways 36 that extend downward and downstream through separation plate 10 to second surfaces 10b. As more fully described below, orifices 34 and passageways 36 are provided merely as one example of a major flow outlet and, thus, may be replaced with any other suitable major flow outlet.

Figure 2A:
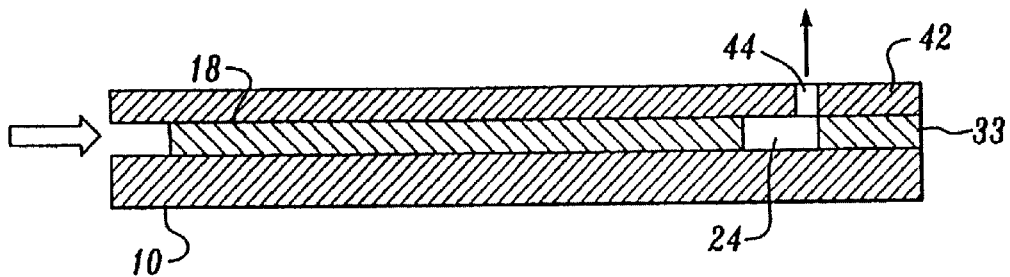
FIG. 2A is a schematic cross-sectional view of a virtual impact collector incorporating another configuration of a separation plate of the present invention.

In operation, particle laden fluid stream 23 is caused to enter inlet ends 14a of nozzles 14. Nozzles 14 aerodynamically focus and accelerate particles entrained in fluid stream 23. In this telescoping design, the aerodynamically focused fluid stream 23 exiting outlet ends 14b of nozzles 14 advances to convex surfaces 31 of virtual impactors 16. A major portion (at least 50%, preferably at least approximately 90%) of fluid stream 23 containing a minor portion (less than about 50%) of particles above a certain particle diameter size, or a "cut size," hereinafter referred to as a "major flow," changes direction to avoid obstruction presented by convex surfaces 31. Concave walls 22 of nozzle projections 18 and convex outer walls 28 of fin-shaped projections 24 cooperate to direct the major flow toward the upstream end of virtual impactor bodies 33. Bodies 33 prevent the major flow from further advancing. When orifices 34 are provided through bodies 33, the major flow enters orifices 34 and travels through passageways 36 to second surface 10*b* of separation plate 10, where it can be exhausted or processed further. A minor portion (less than 50%, preferably less than approximately 10%) of fluid stream 23 containing a major portion (at least about 50%) of particles above the "cut size," hereinafter "minor flow," is collected near a "dead fluid" zone or a zone of nearly stagnant air created adjacent to the convex surfaces 31 of virtual impactors 16. The major portion of the particles entrained in the minor flow "virtually" impact the virtual impact voids, or the inlet ends 32 of upstream minor flow passages 30*a*, and enter the minor flow passages 30. The minor flow travels through minor flow passages 30 and exits therefrom, enabling the particles entrained therein to be collected, analyzed, or processed further.

Nozzles 14 contribute very little to particle loss because they have a long telescoping profile, which prevents particle deposition thereon. The long telescoping profile of the nozzles 14 also serves to align and accelerate particles. Focusing the particles before they enter the minor flow passage using the telescoping design may enhance the performance of the virtual impactor, since the particles in the center of the nozzle are likely to remain entrained in the minor flow. Thus, as used herein, the term "aerodynamic focusing" refers to a geometry of a particle separator that concentrates particles toward the center of a central channel through the particle separator. Because nozzles 14 aerodynamically focus and accelerate particles in a fluid stream, virtual impactors 16 placed downstream of nozzles 14 are able to separate particles very efficiently. By improving the particle separation efficiency of each of virtual impactors 16, the present invention allows for employing only one layer or row of virtual impactors 16 for completing particle separation, which eliminates the chances of particles getting lost due to impact on surfaces of additional layers or rows of virtual impactors. The present invention further reduces particle loss on inner surfaces of minor flow passages, by allowing minor flows to advance straight through the minor flow passages upon virtual impaction, without having to change their flow direction.

A separation plate 10 configured in accordance with the dimensions (all in inches) shown in FIGS. 1A and 1B is designed to have a cut size of 1.0 microns at a flow rate of 35 liters per minute (LPM). The term "cut size" means a particle diameter at which 50% of the particles of that diameter flowing along the first surface of a separation plate are separated from a fluid stream and mostly exhausted through the minor flow passages. For particles having a diameter above the cut size, preferably more than 50% of the particles flowing along the separation plate are separated. It should be understood that those skilled in the art may readily optimize separation plate 10 of the present invention to meet a specific "cut size" requirement at a predefined flow rate. For example, the "cut size" of a separation plate may be modified by scaling up or down the various structures provided on the separation plate; larger nozzles with proportionally larger virtual impactors are useful in separating larger particles, while conversely smaller nozzles with proportionally smaller virtual impactors are useful in separating smaller particles. The "cut size" of a separation plate may also be modified by adjusting a flow rate through the separation plate. For particles having 1- to 3-micron diameters, it has been found that making "a" greater than "b" generally reduces recirculation of a minor flow upon entering minor flow passage 30, which is preferable for efficiently separating a minor flow from a major flow. For larger particles, it may be preferable to make "b" larger than "a" to reduce pressure drop.

FIG. 1D illustrates modified configurations of a nozzle 14 and a virtual impactor 16, wherein inner walls 26 of fin-shaped projections 24 include a generally concave surface. Accordingly, the width of upstream minor flow passage 30*a* expands from inlet end 32 toward downstream minor flow passage 30*b*, which is defined between the external walls of adjacent virtual impactor bodies 33. This configuration is advantageous in reducing particle loss onto inner walls 26.

A separation plate of the present invention may be easily modified to process virtually any volume of fluid stream at any flow rate, by varying the number of nozzles 14 and virtual impactors 16 provided on the separation plate. Furthermore, the throughput of separation plate 10 may be almost indefinitely modifiable by increasing or decreasing height "H" of nozzles 14, virtual impactors 16, and virtual impactor bodies 33. It should be noted that height "H" of a separation plate of the invention can be freely increased without a significant increase in particle loss. This capability is made possible by the present design that allows minor flows to advance straight through without experiencing any deflected path.

Separation plate 10 of the present invention may be readily incorporated into various particle separation/ concentration apparatus. Referring to FIG. 2A, for example, a virtual impact collector may be formed by placing a cover plate 42 over projections 18, fin-shaped projections 24, and virtual impactor bodies 33 provided on first surface 10a. Cover plate 42 and first surface 10a cooperatively define a chamber. Inlet ends 14a of nozzles 14 provide an inlet through which a particle-laden fluid stream may enter the chamber. Minor flow passages 30 provide an outlet through which a minor flow may exit the chamber; however, an outlet through which a major flow may exit the chamber may be provided in various other ways. For example, as in FIGS. 1A and 1B, a plurality of orifices 34 defining terminal ends of passageways 36 may be provided through virtual impactor bodies 33. Alternatively, as in FIG. 2, cover plate 42 may include a plurality of holes 44 that extend therethrough. Holes 44 are configured and arranged so that when cover plate 42 is mated with separation plate 10, holes 44 are disposed between virtual impactors 16 and adjacent to the upstream end of virtual impactor bodies 33, to exhaust major flows flowing around virtual impactors 16 that are blocked by bodies 33, as indicated by an arrow. It should be understood that, in operating the virtual impact collector as described above, those skilled in the art can provide a suitable flow subsystem for causing a fluid stream to flow through the chamber.

Figure 2B:
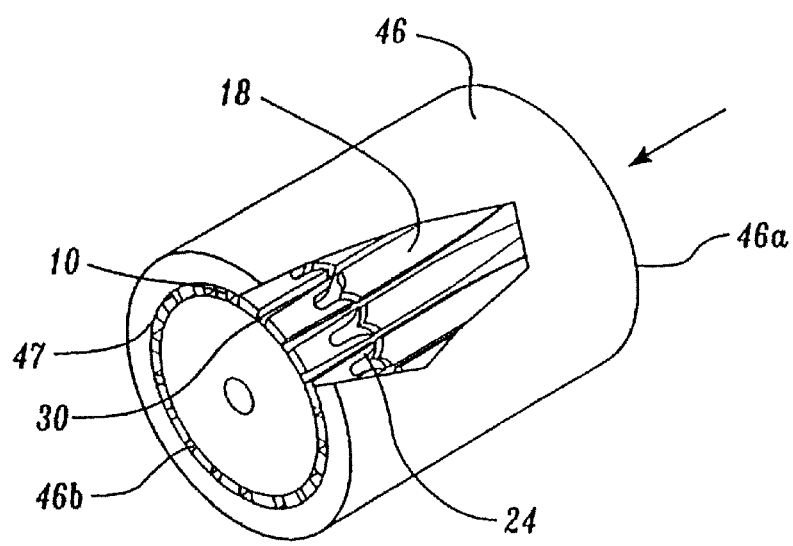
FIG. 2B is a schematic perspective view of an alternative configuration of a virtual impact collector in accordance with the present invention.

A further example of a virtual impact collector formed in accordance with the present invention is schematically illustrated in FIG. 2B. In this embodiment, separation plate 10 of FIG. 1A is joined at its opposing edges 45 to form a cylinder. The second surface of separation plate 10 forms the inner surface of the cylinder. The cylindrical separation plate 10 is coaxially slid into a tube 46 having two open ends 46a and 46b to form an annular chamber 47 therebetween. As before, a suitable major flow outlet is provided (not shown). In operation, particle-laden fluid streams enter chamber 47 through the inlet ends of the nozzles defined between nozzle projections 18, adjacent to open end 46a. Minor flow passages 30 provide an outlet through which a minor flow may exit chamber 47. A suitably provided major flow outlet deflects a major flow to either or both of the inner surfaces of the cylindrical separation plate 10 and/or the outer surface of tube 46.

Figure 3A:
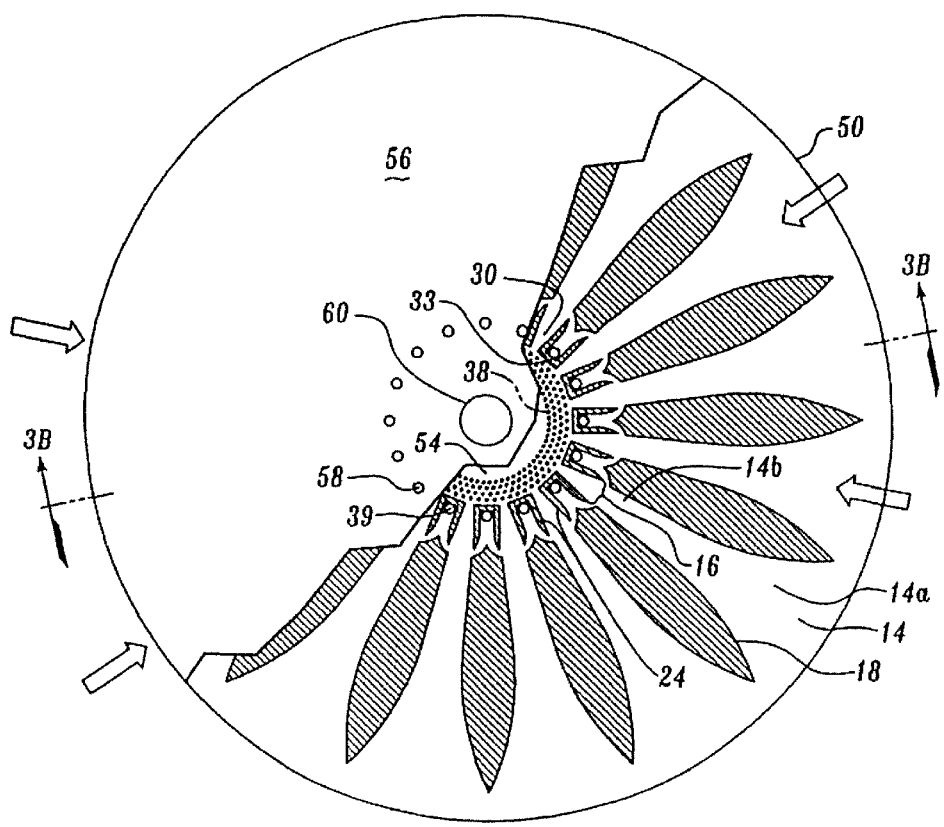
FIG. 3A is a plan view of a virtual impact collector incorporating plural pairs of a nozzle and a virtual impactor arranged radially.
Figure 3B:
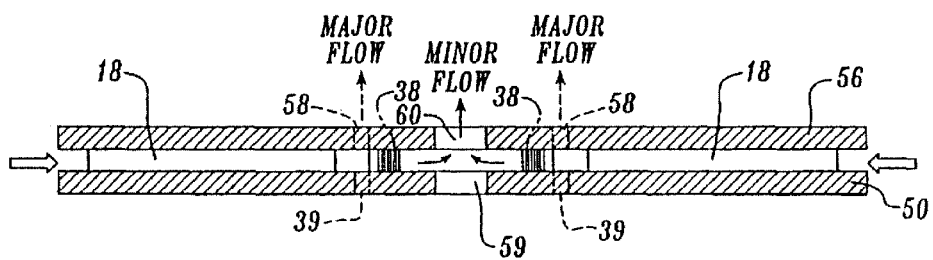
FIG. 3B is a cross-sectional view of the virtual impact collector taken along line 3B—3B of FIG. 3A.

FIGS. 3A and 3B schematically illustrate a virtual impact collector 10 incorporating another configuration of a separation plate 50 of the present invention and a cover plate 56. Separation plate 50 includes plural pairs of nozzles 14 and virtual impactors 16; the virtual impactors are disposed radially inward of nozzles 14. As before, nozzle 14, which has an inlet end 14a and an outlet end 14b, is defined between adjacent nozzle projections 18. Virtual impactor 16 comprises a pair of fin-shaped projections 24 provided downstream of, and radially inward of, outlet end 14b of each nozzle 14. As before, fin-shaped projections 24 in each pair are spaced apart and define minor flow passage 30 therebetween. Also as before, a plurality of virtual impactor bodies 33 in the form of a wall extend between the downstream ends of fin-shaped projections 24 of adjacent virtual impactors 16. Optionally, a plurality of holes 39 may be provided through separation plate 50 radially outward of virtual impactor bodies 33 and between fin-shaped projections 24 of adjacent virtual impactors 16. Virtual impactors 16 and bodies 33 together define a central minor flow collection portion 54. A plurality of impactor pillars 38 may be placed radially inward and downstream of minor flow passages 30, within central minor flow collection portion 54. Impactors 38 are employed to receive a minor flow and to collect particles thereon, as more fully described below.

Optionally, a minor flow outlet 59 may be provided through separation plate 50 near the center of central minor flow collection portion 54. Separation plate 50, which is described above, may be combined with cover plate 56 to form a virtual impact collector. Cover plate 56 is configured to mate with separation plate 50 to define a chamber therebetween. Optionally, cover plate 56 may include holes 58 that are configured and arranged so that when separation plate 50 and cover plate 56 are combined, holes 58 are aligned to coincide with holes 39 defined through separation plate 50. Further optionally, cover plate 56 may include a minor flow outlet 60 defined therethrough. Minor flow outlet 60 is configured so that when cover plate 56 and separation plate 50 are combined, minor flow outlet 60 of cover plate 56 aligns with minor flow outlet 59 of separation plate 50. Holes 39 of separation plate 50 and/or holes 58 of cover plate 56 provide a major flow outlet to the chamber. Minor flow outlet 59 of separation plate 50 and/or minor flow outlet 60 of cover plate 56 provide a minor flow exhaust to the chamber.

In operation, particle-laden fluid streams enter nozzles 14 through inlet ends 14a and advance radially inward. When aerodynamically focused fluid streams advance toward virtual impactors 16, they are separated into a minor flow and a major flow, as described above. The major flow flows around virtual impactors 16, is blocked by bodies 33, and is exhausted through either or both of holes 39 in separation plate 50 and/or holes 58 in cover plate 56. The minor flow advances through minor flow passages 30 into central minor flow collection portion 54. When impactors 38 are provided, some of the particles entrained in the minor flow may impact and become deposited on impactors 38. The particles collected on impactors 38 may be subsequently collected, for example, by washing impactors 38 with a small amount of liquid to capture the particles therein. An example of impactors suitable for use in conjunction with the present invention can be found in copending U.S. patent application, Ser. No. 09/191,979, filed Nov. 13, 1998, concurrently with the parent case hereof, and assigned to the same assignee, which is herein expressly incorporated by reference. The minor flow may be exhausted from central minor flow collection portion 54 through either or both of minor flow outlets 59 and 60.

When both minor flow outlets 59 and 60, and both holes 39 and 58 are provided, as illustrated in FIG. 3B, a plurality of the virtual impact collectors described above may be stacked together to process large amounts of fluid streams. The stacked virtual impact collectors include a common minor flow exhaust conduit comprising minor flow outlets 59 and 60, and a common major flow exhaust conduit comprising holes 39 and 58.

Figure 4A:
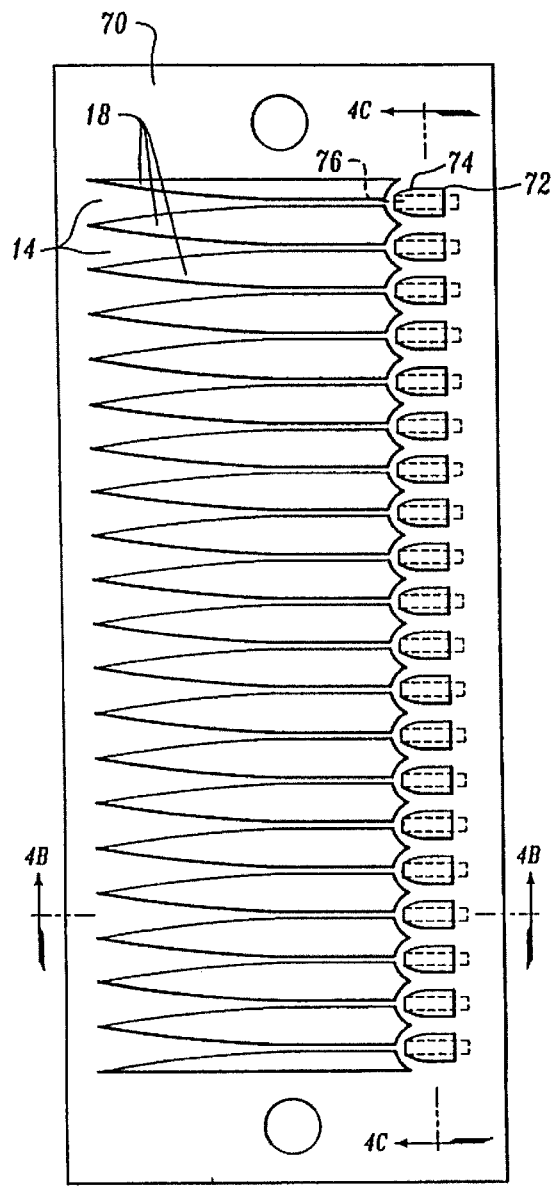
FIG. 4A is a plan view of another configuration of a separation plate in accordance with the present invention.
Figure 4C:
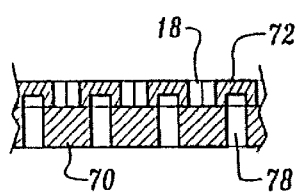
FIG. 4C is a cross-sectional view of the separation plate taken along line 4C—4C of FIG. 4A.
Figure 4B:
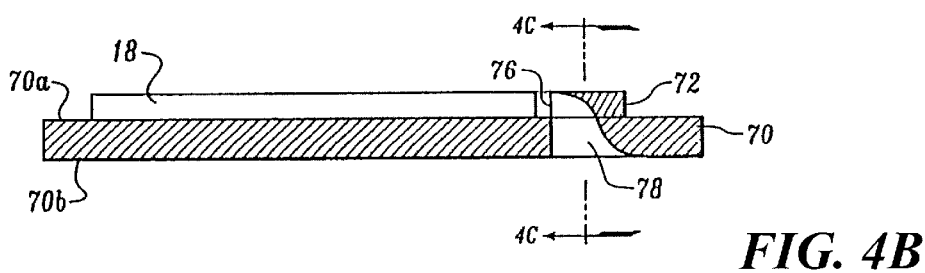
FIG. 4B is a cross-sectional view of the separation plate taken along line 4B—4B of FIG. 4A.

FIGS. 4A, 4B, and 4C illustrate another embodiment of a separation plate 70 in accordance with the present invention. As in the first embodiment, separation plate 70 includes a first surface 70a and an opposing second surface 70b. First surface 70a is provided with a plurality of nozzle projections 18 that define nozzles 14 therebetween. As before, nozzle 14 tapers from an inlet end 14a to an outlet end 14b. Downstream of each outlet end 14b, a generally haystack-shaped virtual impactor projection 72 is provided. Virtual impactor projection 72 includes a convex leading surface 74 facing the fluid flow. A virtual impact void 76 is provided through convex surface 74 near its apex. Virtual impact void 76 defines a terminal end of a minor flow passage 78 that extends down and through separation plate 70. Minor flow passage 78 and virtual impact void 76 may be formed by, for example, boring an end-mill through second surface 70b of separation plate 70. Alternatively, minor flow passage 78 and virtual impact void 76 may be formed by drilling a hole through separation plate 70. When drilling a hole, minor flow passage 78 preferably passes through separation plate 70 at an acute angle so that a minor flow containing a major portion of particles will avoid sharp changes in direction upon entering virtual impact void 76. It should be noted that the longer the minor flow passage 78, the more particles may be deposited on the inner surfaces of minor flow passage 78. Therefore, while the angle of minor flow passage 78 should be as acute as possible, the length of minor flow passage 78 cannot be indefinitely long. The optimum combination of the angle and the length of minor flow passage 78 is to be determined based partly on the limitations imposed by the available micromachining methods. An angle of between approximately 15° and 45°, which is possible with currently available micromachining methods, should provide satisfactory results.

In operation, particle-laden fluid streams flow along first surface 10a through nozzles 14 and advance toward convex surfaces 74 of virtual impactor projections 72. Major flows flow around projections 72 to avoid obstruction presented by convex surfaces 74, and continue along first surface 10a. Minor flows are collected in a zone of stagnant fluid created near convex surfaces 74, and enter virtual impact voids 76 defined through convex surfaces 74. The minor flows travel through minor flow passages 78 to second surface 70b, where they can be collected, analyzed, or processed further in any other manner desired. Thus, unlike separation plates 10 and 50 of the previous embodiments, separation plate 70 of the present embodiment separates a particle-laden fluid stream into a minor flow on the second surface, and a major flow on the first surface.

Figure 5A:
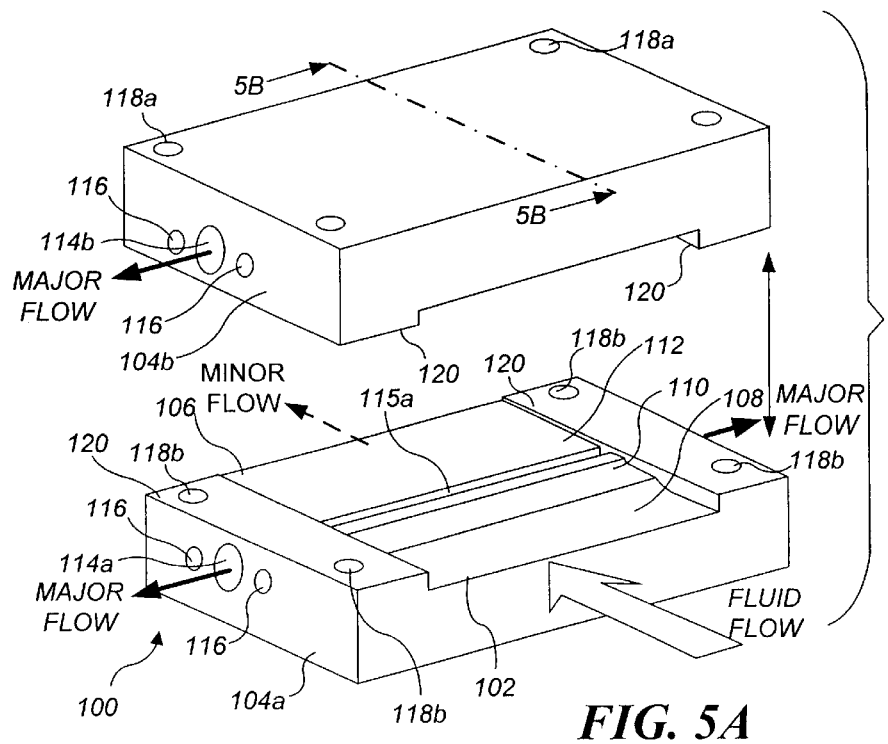
FIG. 5A is an isometric view of yet another alternative embodiment of a separation plate in accord with the present invention.
Figure 5B:
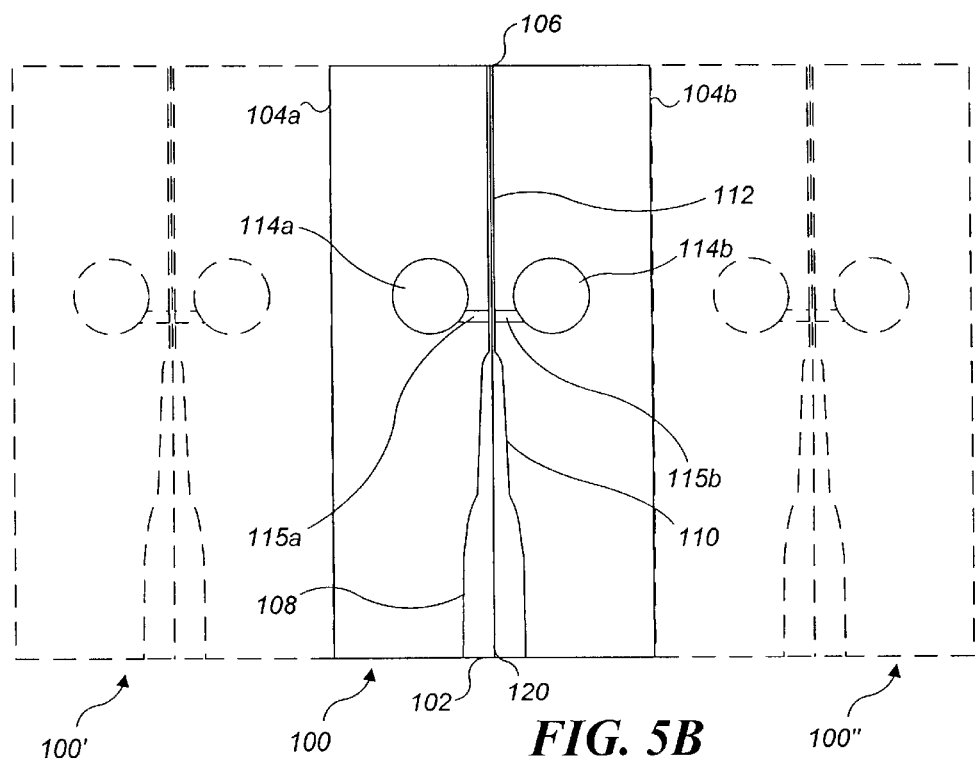
FIG. 5B is a cross-sectional view of the separation plate of FIG. 5A, showing additional separation plates arrayed on each side in phantom view.

Another embodiment of a separation plate 100 is illustrated in FIGS. 5A and 5B. Separation plate 100 includes a central passage 102 that extends laterally across the length of the separation plate and through its width. The passage is defined between plates 104a and 104b and is machined within the facing surfaces of these two plates, which preferably comprise a metal such as steel, aluminum, or titanium, or another suitable material such as plastic. Alternatively, the passage can be formed by molding or casting the plates from metal, or another suitable material, such as plastic. Passage 102 is readily formed in the surfaces of each of plates 104a and 104b by conventional machining techniques. Since the surfaces are fully exposed, the desired telescoping or converging configuration of the passage is readily formed. The passage extends from an inlet 108, which is substantially greater in cross-sectional area due to its greater height than an outlet 106. The outlet is disposed on the opposite side of the separation plate from the inlet. Inlet 108 tapers to a convergent nozzle 110, which further tapers to the opening into a minor flow portion 112 of passage 102.

In this preferred embodiment of separation plate 100, one-half the thickness of passage 102 is formed in plate 104a, and the other half of the thickness of the passage is formed in plate 104b. However, it is also contemplated that the portions of the passage defined in each of plates 104a and 104b need not be symmetrical or identical, since a desired configuration for passage 102 can be asymmetric relative to the facing opposed surfaces of the two plates.

Immediately distal of the point where minor flow portion 112 of passage 102 begins, slots 115a and 115b are defined and extend transversely into the plates relative to the direction between the inlet and the outlet of passage 102 and extend laterally across separation plate 100 between the sides of the passage. Slots 115a and 115b respectively open into major flow outlet ports 114a and 114b, in the ends of plates 104a and 104b, as shown in FIG. 5A. Threaded fastener holes 116 are disposed on opposite sides of each of major flow outlet ports 114a and 114b and are used for connecting a major flow manifold (not shown) that receives the major flow of fluid in which the minor portion of the particles greater than the cut size is entrained.

Fastener holes 118a are formed through plate 104b adjacent to its four corners and do not include threads. Threaded fasteners (not shown) are intended to be inserted through holes 118a and threaded into holes 118b, which are formed at corresponding corner positions on plate 104a. The threaded fasteners thus couple edge seals 120 on the two plates together, sealing the edges of passage 102 and connecting plates 104a and 104b to form separation plate 100. Although not shown, a manifold may also be connected to the back surface of separation plate 100 overlying outlet 106 to collect the minor flow of fluid in which the major portion of particles exceeding the cut size is entrained. In FIG. 5A, the flow of fluid entering inlet 108 of passage 102 is indicated by the large arrow, the major flow exiting major flow ports 114a and 114b is indicated by the solid line arrows, and the minor flow exiting outlet 106 of passage 102 is indicated by the dash line arrow. The cross-sectional profile of passage 102 as shown in FIG. 5B focuses the particle-laden fluid flow entering inlet 106 for delivery to the convergent nozzle and thus performs in much the same way as the profile used in the previous embodiments of virtual impactors.

The desired flow through the separation plate will determine the width of passage 102, as measured along the longitudinal axis of the separation plate, between sealed edges 120. Additional fluid flow can also be accommodated by providing a plurality of the separation plates in an array, which will also avoid using extremely long and thin structures, which may not fit within an available space. FIG. 5B illustrates two such additional separation plates 100' and 100", stacked on each side of separation plate 100, so that the fluid enters the inlets of the stacked separation plates and is separated in the major flow and the minor flow exiting the separations plates as described above.

Figure 6A:
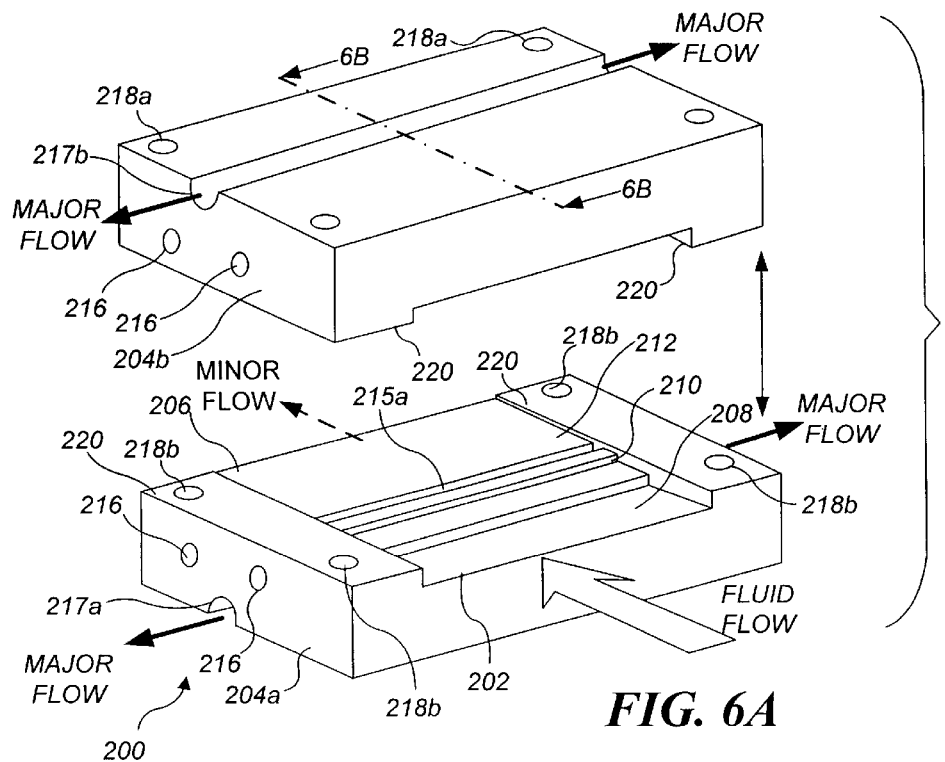
FIG. 6A is an isometric view of still another alternative embodiment of a separation plate in accord with the present invention.
Figure 6B:
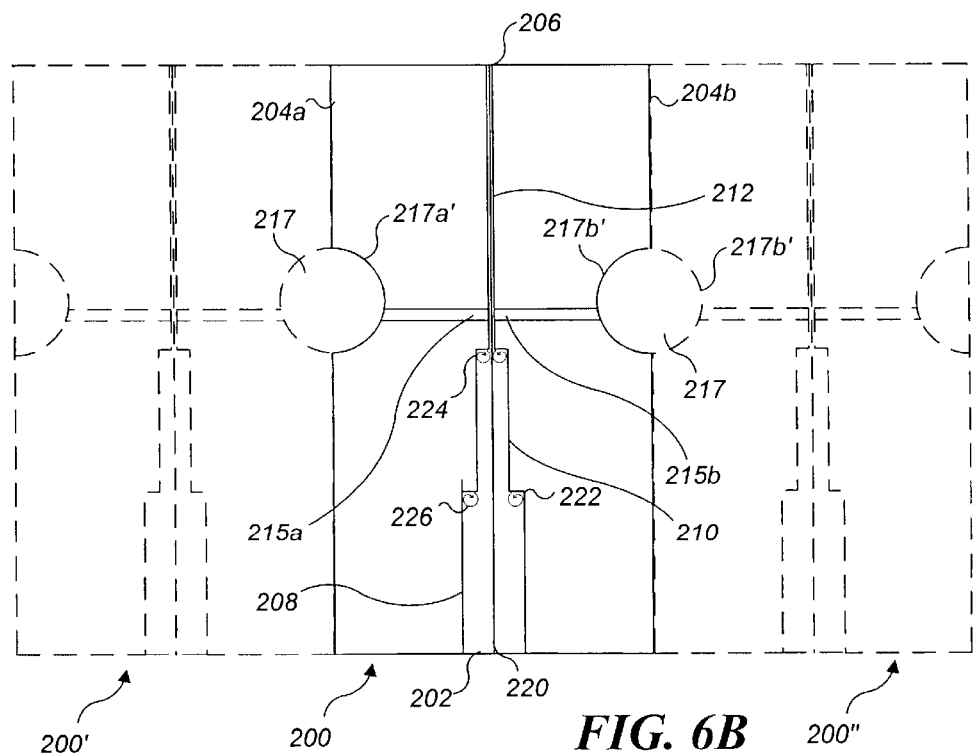
FIG. 6B is a cross-sectional view of the separation plate of FIG. 6A, showing additional separation plates arrayed on each side in phantom view.

FIGS. 6A and 6B illustrate still another embodiment of a separation plate 200 that is similar to separation plate 100, which was discussed above in regard to FIGS. 5A and 5B. Separation plate 200 differs from separation plate 100 in at least two significant ways, as will be apparent from the following discussion. To simplify the following disclosure of separation plate 200, the reference numbers applied to its elements that are similar in function to those of separation plate 100 are greater by 100. Thus, like central passage 102 in separation plate 100, separation plate 200 includes a central passage 202 that extends laterally across the length of the separation plate and through its width. The passage is defined between plates 204a and 204b and is machined within the facing surfaces of these two plates, which also preferably comprise a metal such as steel, aluminum, or titanium formed by machining or by molding the plates from metal, or another suitable material, such as a plastic. The passage extends from an inlet 208, which is substantially greater in cross-sectional area due to its greater height to an outlet 206 disposed on the opposite side of the separation plate from the inlet. Unlike inlet 108 of the previous embodiment, which tapers to a convergent nozzle 110 and then to a minor flow portion 112 of passage 102, the central passage in separation plate 200 does not taper to smaller cross-sectional sizes. Instead, the central passage in separation plate 200 changes abruptly to a smaller cross-sectional size at a step 222, continuing through a section 210, and then again steps abruptly to a smaller minor flow outlet 212, at a step 224. At each of steps 222 and 224, a swirling flow or vortex 226 of the fluid is produced. It has been empirically determined that these vortexes tend to focus the particles toward the center of the passage, thereby providing a substantial improvement in the efficiency with which the particles smaller than the cut size are separated from the particles larger than the cut size.

In this preferred embodiment of separation plate 200, one-half the thickness of passage 202 is formed in plate 204a, and the other half of the thickness of the passage is formed in plate 204b, just as in the previous embodiment. And again, it is contemplated that the portions of the passage defined in each of plates 204a and 204b need not be symmetrical or identical, since a desired configuration for passage 202 can be asymmetric relative to the facing opposed surfaces of the two plates.

Immediately distal of the point where minor flow portion 212 of passage 202 begins, slots 215a and 215b are defined and extend transversely into the plates relative to the direction between the inlet and the outlet of passage 202 and extend laterally across separation plate 200 between the sides of the passage, just as in separation plate 100. Slots 215a and 215b respectively open into major flow outlet ports 217a and 217b, which are open to the ends and outer surfaces of plates 204a and 204b, as shown in FIG. 6A. In this embodiment, separation plate 200 is designed to be stacked with other similar separation plates 200' and 200", as shown in FIG. 6B, so that adjacent separation plates cooperate in forming the passage for conveying the major flow into an overlying major flow manifold (not shown). It is also contemplated that separation plate 100 can be configured to include major flow outlet ports similar to those in separation plate 200. The last plate disposed at the top and bottom of a stack of separation plates configured like those in FIG. 6B would include major flow outlet ports 114a and 114b, respectively. Threaded fastener holes 216 are disposed on opposite sides of each of major flow outlet ports 217a and 217b and are used for connecting a major flow manifold (not shown) that receives the major flow of fluid in which the minor portion of the particles greater than the cut size is entrained.

Fastener holes 218a are formed through plate 204b adjacent to its four corners and do not include threads. Threaded fasteners (not shown) are intended to be inserted through holes 218a and threaded into holes 218b, which are formed at corresponding corner positions on plate 204a. The threaded fasteners thus couple edge seals 220 on the two plates together, sealing the edges of passage 202 and connecting plates 204a and 204b to form separation plate 200. Although not shown, a manifold may also be connected to the back surface of separation plate 200 overlying outlet 206 to collect the minor flow of fluid in which the major portion of particles exceeding the cut size is entrained. In FIG. 6A, the flow of fluid entering inlet 208 of passage 202 is indicated by the large arrow, the major flow exiting major flow ports 217a and 217b is indicated by the solid line arrows, and the minor flow exiting outlet 206 of passage 202 is indicated by the dash line arrow.

Separation plates 100 and 200 costs less to manufacture than the other embodiments discussed above. As was the case with separation plate 100, the desired flow through the separation plate will determine the width of passage 202 along the longitudinal axis of the separation plate, between sealed edges 220, and additional fluid flow can also be accommodated by providing a plurality of the separation plates in an array configured to fit within an available space. FIG. 6B illustrates two additional separation plates 200' and 200", stacked on opposite sides of separation plate 200, so that the fluid enters the inlets of the stacked separation plates and is separated in the major flow and the minor flow exiting the separations plates, as described above.

Figure 7:
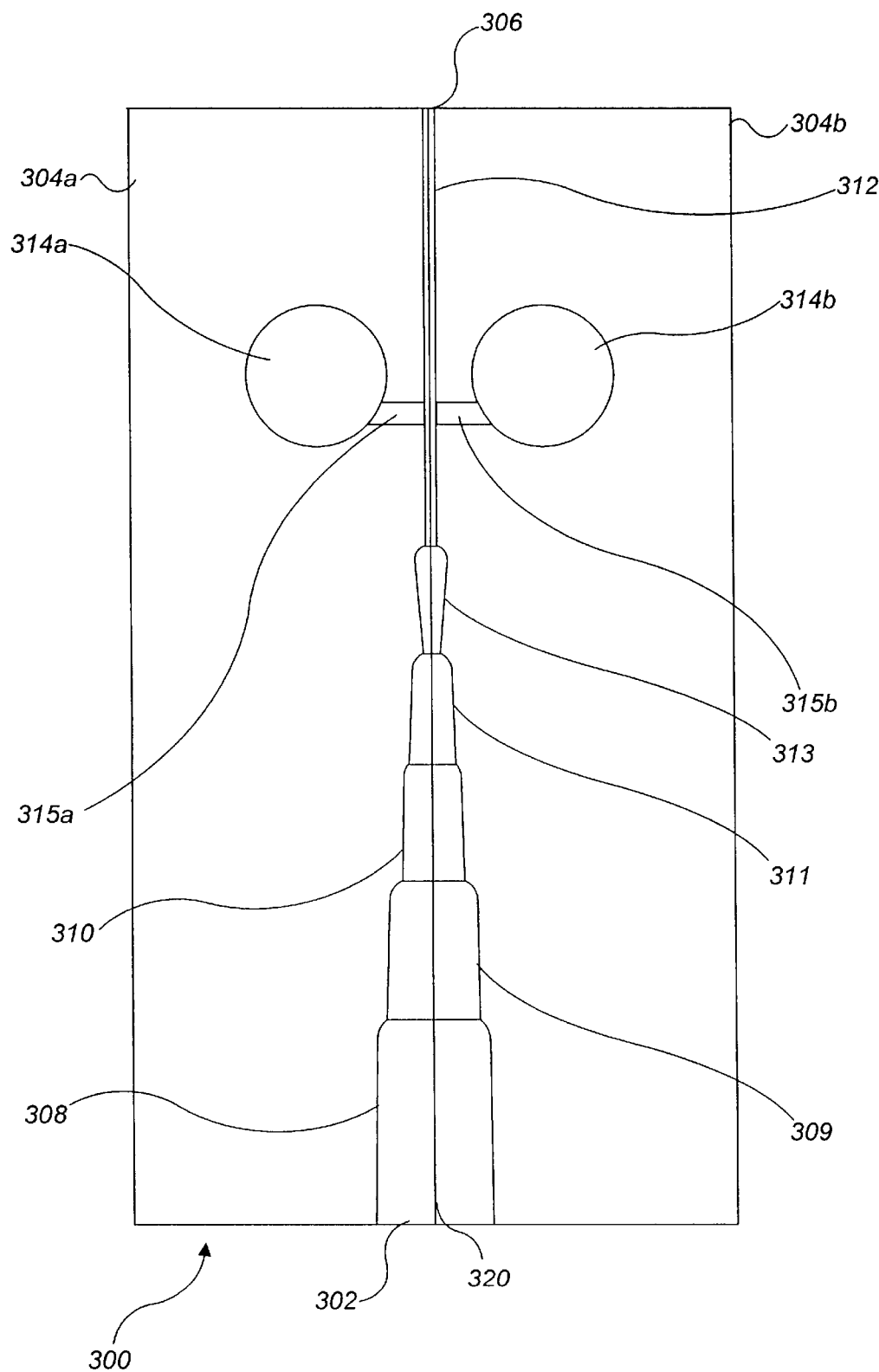
FIG. 7 is a cross-sectional view of a separation plate like that shown in FIGS. 5A and 5B, but having a slightly modified passage through which the fluid flows to optimize the efficiency of separation over a broader range of particle sizes.

Finally, yet another embodiment of the present invention, a separation plate 300 is illustrated in FIG. 7. Separation plate 300 is also similar to separation plate 100, which is shown in FIGS. 5A and 5B, but includes a central passage 302 that differs from central passage 102 in separation plate 100. Again, to simplify the following discussion, reference numbers are applied to the elements of separation plate 300 that are similar in function to those of separation plate 100 are simply made greater by 200. It will thus be apparent that central passage 102 in separation plate 100 corresponds to central passage 302 in separation plate 300 and that central passage 302 extends laterally across the length of separation plate 300 and through its width. The passage is defined between plates 304a and 304b and is machined within the facing surfaces of these two plates, preferably from a metal such as steel, aluminum, or titanium formed by machining, or by molding the plates from metal, or another suitable material, such as a plastic. The passage extends from an inlet 308, which is substantially greater in cross-sectional area due to its greater height, to an outlet 306 disposed on the opposite side of the separation plate from the inlet. Central passage 302 comprises a telescoping section that performs aerodynamic focusing of the particles so as to achieve a further optimization in maximizing the efficiency of the separation plate over a wider range of particles sizes, compared to the other embodiments. The focusing is accomplished in this embodiment by using a combination of contracting and diverging sections. Specifically, an inlet 308 tapers slightly at its distal end to a more convergent section 309, which again tapers to a convergent nozzle 310, which further tapers at its distal end to another convergent section 311. The distal end of convergent section 311 tapers into the proximal end of a divergent section 313, and its distal end then tapers into a minor flow portion 312 of central passage 302. Distal of the point where minor flow portion 312 of central passage 302 begins, slots 315a and 315b are defined and extend transversely into the plates relative to the direction between the inlet and the outlet of central passage 302 and extend laterally across separation plate 300 between the sides of the passage. Major flow outlet ports 314a and 314b can be used for connecting to a major flow manifold (not shown) that receives the major flow of fluid in which the minor portion of the particles greater than the cut size is entrained.

As will be apparent from the preceding description, a number of gentler steps are used in the central passage of separation plate 300 than in the preceding embodiments of FIGS. 5A and 5B, and 6A and 6B, to improve the efficiency of separating larger particles (i.e., approximately $5\mu$ to $10\mu$ in size); larger particles tend to have greater wall losses due to impaction on the "steps" of the telescoping profile. The gentler steps will not focus the small particles as well as in the other embodiments, however, so the outward expansion provided by diverging section 313, followed by a final steep step into minor flow passage 312 to focus the small particles seems to improve the efficiency of the separation (at least in simulations). The larger particles do not expand out much in diverging section 313, and are thus less likely to be impacted on the final step into minor flow passage 312.

In all other respects, separation plate 300 operates like separation plate 100, and can be modified to collect the major flow like separation plate 200. It will also be apparent that a plurality of separation plates 300 can be stacked, just as the previous embodiments, to increase the volume of fluid processed.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A separation plate employed for separating a fluid stream into a major flow and a minor flow, the major flow including a minor portion of particles that are above a predetermined size and the minor flow including a major portion of the particles that are above the predetermined size, said separation plate comprising:

(a) a block in which is defined a laterally extending passage having an inlet disposed on one edge of the block and an outlet disposed on an opposite edge of the block, said passage having a length extending between said inlet and said outlet, a lateral dimension extending in a direction that is orthogonal to the length and to a transverse dimension extending between the opposed surfaces of the laterally extending passage, said lateral dimension being substantially greater than the transverse dimension of the passage, the opposed surfaces of said passage between which the transverse dimension of the passage is defined generally converging toward each other within the block;

(b) a transverse, laterally extending slot defined within said block, in fluid communication with a portion of the passage that has the substantially smaller cross-sectional area; and (c) a major flow outlet port defined in the block, in fluid communication with the transverse, laterally extending slot, the major flow entering the slot and exiting the block through the major flow outlet port, while the minor flow exits the block through the outlet of the passage, said major flow carrying the minor portion of the particles, and said minor flow carrying the major portion of the particles that are above the predetermined size.

2. The separation plate of claim 1, further comprising another transverse, laterally extending slot that is disposed opposite the slot within the block; and another major flow outlet port in fluid communication with the other slot, said other major flow outlet port also providing a fluid path for the major flow carrying the minor portion of the particles.

3. The separation plate of claim 1, wherein the block comprises a first plate and a second plate that are coupled together, said passage being defined between facing surfaces of the first plate and the second plate.

4. The separation plate of claim 3, wherein the facing surfaces of the first plate and the second plate are joined at each end of the passage, sealing the ends of the passage.

5. The separation plate of claim 4, wherein a portion of the passage is defined in a facing surface of the first plate, and a portion of the passage is defined in a facing surface of the second plate.

6. The separation plate of claim 1, wherein the passage converges with a defined transverse profile toward a convergent nozzle at an entrance to a minor flow portion of the passage, the transverse, laterally extending slot being disposed distally of but proximate to the convergent nozzle.

7. The separation plate of claim 1, wherein a lateral dimension of the passage is a function of a desired flow of fluid through the inlet of the passage.

8. The separation plate of claim 1, wherein a profile of the passage includes at least one step prior to the portion of the passage that has the substantially smaller cross-sectional area.

9. The separation plate of claim 1, wherein the passage includes a plurality of steps prior to the portion of the passage that has the substantially smaller cross-sectional area, at least one step converging and at least one step at least partially diverging.

10. Apparatus for separating a fluid flow in which particles are entrained, into a major flow that includes a minor portion of particles above a predetermined size and a minor flow that includes a major portion of the particles above the predetermined size, comprising:

(a) a block having a front and a rear;
    (b) a laterally extending passage defined within the block and extending between an inlet at the front and an outlet at the rear of the block, said passage converging to a convergent nozzle between the inlet and the outlet, the inlet having a substantially greater height than a maximum height of the convergent nozzle, and the maximum height of the convergent nozzle being substantially less than a width of the passage;
    (c) an elongate slot extending transverse to the passage and disposed distally of the convergent nozzle; and
    (d) a major flow orifice formed within the block and intersecting the slot, said major flow orifice providing a fluid path for the major flow to exit the block after changing direction, the minor flow continuing on and out of the outlet of the passage, so that the major portion of the particles above the predetermined size are carried with the minor flow through the outlet of the passage, while the minor portion of the particles above the predetermined size are carried with the major flow through the major flow orifice.

11. The apparatus of claim 10, further comprising another elongate slot extending transverse to the passage and disposed distally of the convergent nozzle, generally opposite the slot, and another major flow orifice formed within the block and intersecting the other slot, said other major flow orifice providing another fluid path for the major flow to exit the block after changing direction.

12. The apparatus of claim 11, wherein the block comprises a first plate having a portion of the passage defined in a surface thereof, and a second plate having a portion of the passage defined in a surface thereof, said first plate and said second plate being coupled together with the surfaces in which the portions of the passage are defined facing each other.

13. The apparatus of claim 12, wherein the slot and the major flow orifice are formed in the first plate and the other slot and the other major flow orifice are formed in the second plate.

14. The apparatus of claim 13, wherein the first plate and the second plate provide seals along edges of the passage, when the first plate is coupled to the second plate.

15. The apparatus of claim 14, wherein a width of the passage between the seals along the edges is determined as a function of a desired fluid flow through the passage.

16. The apparatus of claim 10, wherein the minor portion includes less than 50% of the particles above the predetermined size.

17. The apparatus of claim 10, wherein the minor portion includes less than 10% of the particles above the predetermined size.

18. The apparatus of claim 10, further comprising at least another block, each other block having:
(a) a front and a rear;
(b) a laterally extending passage defined therein and extending between an inlet at the front and an outlet at the rear thereof, said passage forming a convergent nozzle between the inlet and the outlet, the inlet having a substantially greater height than a maximum height of the convergent nozzle, and the maximum height of the convergent nozzle being substantially less than a width of the passage in the other block;
(c) an elongate slot extending transverse to the passage in the other block; and
(d) a major flow orifice formed within each other block and intersecting the slot therein, said block and each other block being assembled in an array of blocks that separates the major flow from the minor flow.

19. The apparatus of claim 10, wherein a profile of the laterally extending passage includes at least one step disposed upstream of the elongate slot, said at least one step tending to focus the particles toward a center of the laterally extending passage.

20. The apparatus of claim 19, wherein the profile includes at least one step that diverges over at least a portion of the profile.

21. The apparatus of claim 10, wherein at least a portion of said convergent nozzle is non convergent.

22. A method for separating a fluid flow in which particles are entrained, into a major flow that includes a minor portion of particles above a predetermined size and a minor flow that includes a major portion of the particles above the predetermined size, comprising the steps of:
(a) directing the fluid flow into a laterally extending passage having a width, an inlet and an outlet, a portion of said laterally extending passage converging toward a convergent nozzle disposed between the inlet and the outlet, said width of said laterally extending passage being substantially greater than a height of the convergent nozzle;
(b) providing a slot transverse to the passage and disposed distal of the convergent nozzle, but proximate thereto;
(c) receiving the minor flow of the fluid in which the major portion of the particles is entrained, from the outlet of the passage; and
(d) receiving the major flow of the fluid in which the minor portion of the particles is entrained from a port coupled in fluid communication with the slot.

23. The method of claim 22, further comprising the step of providing another slot that extends transverse to the passage, and receiving the major flow of the fluid from another port coupled in fluid communication with the other slot.

24. The method of claim 22, wherein the passage is formed between opposed surfaces of a first plate and a second plate that are joined together.

25. The method of claim 22, further comprising the step of selecting a width of the passage as a function of a desired fluid flow therethrough.

26. The method of claim 22, wherein the major flow contains substantially less than 50% of the particles above the predetermined size.

27. The method of claim 22, further comprising the step of providing an array of flow separators, each including the laterally extending passage, the slot, and the major flow port, so that the flow of the fluid is directed into inlets of each passage, the major flow is collected from the major flow port of each flow separator, and the minor flow exits the outlet of each passage.

28. The method of claim 22, further comprising the step of providing at least one step in the passage, upstream of the convergent nozzle, each such step producing a vortex in the fluid flow in which the particles are entrained that focuses the particles toward a center of the passage.

29. The method of claim 22, further comprising the step of providing a plurality of stepped sections in the passage upstream of the convergent nozzle, at least one stepped section converging, and at least one stepped section diverging over at least a portion of the passage.

30. A separation plate employed for separating a fluid stream into a major flow and a minor flow, the major flow including a minor portion of particles that are above a predetermined size and the minor flow including a major portion of the particles that are above the predetermined size, said separation plate comprising:
(a) a block in which is defined a laterally extending passage having an inlet disposed on one edge of the block and an outlet disposed on an opposite edge of the block, said laterally extending passage having a lateral dimension that is substantially greater than a transverse dimension of the passage, opposed surfaces of said passage between which the transverse dimension of the passage is defined generally converging toward each other within the block to define a convergent nozzle having a height substantially smaller than said lateral dimension;
(b) a transverse, laterally extending slot defined within said block, in fluid communication with the convergent nozzle; and
(c) a major flow outlet port defined in the block, in fluid communication with the transverse, laterally extending slot, the major flow entering the slot and exiting the block through the major flow outlet port, while the minor flow exits the block through the outlet of the passage, said major flow carrying the minor portion of the particles and said minor flow carrying the major portion of the particles that are above the predetermined size.

31. The apparatus of claim 30, wherein at least a portion of said convergent nozzle is non convergent.

* * * * *

UNITED STATES PATENT AND TRADEMARK OFFICE
CERTIFICATE OF CORRECTION

PATENT NO. : 6,698,592 B2
APPLICATION NO. : 10/202210
DATED : March 2, 2004
INVENTOR(S) : Kenning et al.

It is certified that error appears in the above-identified patent and that said Letters Patent is hereby corrected as shown below:

| | |
|---|---|
| Column 13, line 35 (Claim 1, line 22) | "the" should read --a-- |
| Column 14, line 22 (Claim 10, line 11) | "maximum" should read --minimum-- |
| Column 14, line 23, (Claim 10, line 12) | "maximum" should read --minimum-- |
| Column 15, line 8 (Claim 18, line 8) | "maximum" should read --minimum-- |
| Column 15, line 9 (Claim 18, line 9) | "maximum" should read --minimum-- |
| Column 16, line 53 (Claim 31, line 1) | "apparatus" should read --separation plate-- |

Signed and Sealed this

Twelfth Day of June, 2007

JON W. DUDAS
*Director of the United States Patent and Trademark Office*

UNITED STATES PATENT AND TRADEMARK OFFICE
CERTIFICATE OF CORRECTION

PATENT NO. : 6,698,592 B2  Page 1 of 1
APPLICATION NO. : 10/202210
DATED : March 2, 2004
INVENTOR(S) : Kenning et al.

It is certified that error appears in the above-identified patent and that said Letters Patent is hereby corrected as shown below:

Column 13, line 35  "the" should read --a--
   (Claim 1, line 22)

Column 16, line 53  "apparatus" should read --separation plate--
   (Claim 31, line 1)

Signed and Sealed this

Tenth Day of July, 2007

JON W. DUDAS
*Director of the United States Patent and Trademark Office*